United States Patent [19]
Ruan et al.

[11] Patent Number: 6,031,135
[45] Date of Patent: Feb. 29, 2000

[54] TRIMETHYLSPHINGOSINE DERIVATIVES

[75] Inventors: Fuqiang Ruan; Yasuyuki Igarashi; Sen-Itiroh Hakomori, all of Seattle, Wash.

[73] Assignee: Oncomembrane, Inc., Seattle, Wash.

[21] Appl. No.: 08/645,191

[22] Filed: May 13, 1996

Related U.S. Application Data

[63] Continuation of application No. 08/095,005, Jul. 23, 1993, abandoned.
[51] Int. Cl.[7] .......................... A61K 31/23; A61K 31/20; A61K 31/14
[52] U.S. Cl. .......................... 564/292; 514/549; 514/561; 514/642; 514/643; 554/109; 564/282; 564/507
[58] Field of Search ..................... 564/282, 292, 564/507; 514/549, 561, 642, 643; 554/109

[56] References Cited

U.S. PATENT DOCUMENTS 5,137,919  8/1992  Igarashi et al. ...................... 514/642

OTHER PUBLICATIONS

Hannun et al. "Lysosphinzolipids Inhibit Protein Kinase C, etc." *Science,* vol. 235, (1987) pp. 670–674.

Merrill, Jr, "Structural Requirements For Long Chain (Sphinzoid) Base Inhibition" *Biochemistry* (1989), 28, 3138–3145.

Endo et al., "Cell Membrane Signaling as Target in Cancer Therapy, etc." *Cancer Research* (1991), 51, pp. 1613–1618.

*Primary Examiner*—Peter O'Sullivan
*Attorney, Agent, or Firm*—Sughrue, Mion, Zinn, Macpeak & Seas

[57] ABSTRACT

The invention relates to trimethylsphingosine derivatives which have some or all of the activities of the parent compound.

6 Claims, 7 Drawing Sheets

SCHEME I  SYNTHESIS OF D-ERYTHRO-N, N-DIMETHYL-N-ETHYL SPHINGOSINE (DMES) AND
D-ERYTHRO-N, N-DIETHYL-N-METHYL SPHINGOSINE (DEMS)

(a) 37% $CH_2O$, $NaCNBH_3$, HOAc-NaOAc BUFFER
(b) (i) $C_2H_5I$, $KHCO_3$, MeOH, (ii) DOWEX 1x2 ($Cl^-$)
(c) $CH_3CHO$, $NaCNBH_3$, HOAc-NaOAc BUFFER
(d) (i) $CH_3I$, $KHCO_3$, MeOH, (ii) DOWEX 1x2 ($Cl^-$)

FIG. 6 SCHEME IV SYNTHESIS OF 3 & 4

TRIMETHYLSPHINGOSINE DERIVATIVES

This is a Continuation of application Ser. No. 08/095,005 filed Jul. 23, 1993 now abandoned.

FIELD OF THE INVENTION

The invention relates to N,N,N-trimethylsphingosine (TMS) derivatives and analogs with a profound effect on protein kinase-C (PK-C or PKC) activity. The TMS derivatives inhibit tumor cell invasiveness, metastatic potential, transendothelial cell migration and platelet activation. The TMS derivatives inhibit inflammatory response of neutrophils and other blood cells, inhibit $O_2$ production, phagokinesis and transendothelial cell migration of neutrophils. The TMS derivatives exert a protective effect on cells, particularly platelets, and hence are useful as a preservative.

BACKGROUND OF THE INVENTION

Sphingosine (SPN) is a long chain unsaturated amino alcohol of the formula $C_{18}H_{37}O_2N$ found in cell membranes and in high concentration in neural tissue. Sphingosine and sphingoid base (a long chain aliphatic base comprising a 1,3-dihydroxy-2-amino group at a terminus and derivatives thereof) have been implicated as inhibitors of protein kinase-C and modulators of EGF receptor-associated tyrosine kinase (EGF-RK) (Hannun & Bell, Science, 235, 670, 1987; Hannun, JBC, 261, 12604, 1986; Kreutter et al., JBC, 262, 1632, 1987).

Protein kinase-C activity is related closely to cell growth and recent studies indicate that increased tumorigenicity is correlated with over expression of PK-$C_{\beta 1}$ and PK-$C_\gamma$ in some experimental tumors (Housey et al., Cell, 52, 343, 1988; Persons et al., Cell, 52, 447, 1988). A mutant PK-$C_\alpha$ induces highly malignant tumor cells with increased metastatic potential (Megidish & Mazurek, Nature, 324, 807, 1989). It would appear that aberrant expression of PK-C may relate to tumor progression.

Recent studies indicate that phospholipids, sphingolipids and metabolic products thereof have an important role in the modulation of transmembrane signaling through PK-C and other membrane-associated kinases, such as EGF receptor-associated tyrosine kinase (Hakomori, JBC, 265, 18713, 1990). For example, PK-C activity is promoted by diacylglycerol and inhibited by sphingosine (Hannun & Bell, supra; Hannun & Bell, Science, 243, 500, 1989; Merrill & Stevens, Biochem. Biophys. Acta, 1010, 131, 1989).

Igarashi et al. (Biochem., 28, 6796, 1989) found that the inhibitory effect of sphingosine on PK-C activity is due to: (1) the stereospecific configuration of $C_2$ to $C_3$ (D-erythro configuration required); (2) presence of a long-chain aliphatic group; and (3) perhaps most essential, a partially negative charge at the primary amino group at $C_2$. If the amino group was N-acetylated, the PK-C inhibitory activity was abolished since the partially negative charge of the amino group was eliminated by acetylation. However if the anionic character of the amino group was enhanced by N-methylation, the stereospecific PK-C inhibitory activity was enhanced.

Interaction of leukocytes with activated platelets and endothelial cells is an initial step in inflammatory processes and is mediated in part by a family of adhesion molecules known as selectins. Selectins include MEL-14 in mouse and ELAM-1, LAM-1 and GMP-140 (CD62/PADGEM) in man. Members of the selectin family bind carbohydrate ligands (see for example, Springer, Nature, 346, 425, 1990; Brandley et al., Cell 63, 861, 1990; Lowe et al., Cell, 63, 475, 1990; and Walz et al., Science, 250, 1132, 1990).

Based on inhibition studies using a variety of glycosphingolipid liposomes, the binding epitopes of both ELAM-1 and GMP-140 expressed on HL60 (a human promyelocytic cell line) cells were identified as sialosyl-Le$^x$ (Phillips et al., Science, 250, 1130, 1990).

Expression of selectins is up-regulated by the inductive effect of lymphokines, tumor necrosis factor (TNFα), bacterial lipopolysaccharides phorbol esters, thrombin and perhaps many other compounds. Leukocytes, together with platelets, thereby are recruited to the inflammatory site.

Since tumor cells are capable of activating platelets (see for example, Ugen et al., J. Natl. Canc. Inst., 80, 1461, 1988; Watanabe et al., Canc. Res., 48, 6411, 1988; and Grignani & Jamieson, Blood, 71, 844, 1988), a similar process can be expected to occur during tumor cell adhesion on microvascular endothelia. Thus, the process of tumor cell metastasis may be initiated by selectin-dependent tumor cell adhesion. Although there is no evidence of direct activation of endothelial cells by tumor cells, IL-1 or TNFα-activated endothelial cells have been shown to adhere to a variety of tumor cells (Walz et al. supra).

While the regulatory mechanism for expression of selectins is understood poorly, it apparently involves a complex sequence of transmembrane signaling transducers including protein kinase-C, members of the G-protein family (for example, ras, $G_s$, $G_i$, $G_0$ etc.) and a 47 kDa phosphoprotein, all of which have been shown to be modulated by glycosphingolipids and sphingosine derivatives. Platelet aggregation and associated ATP secretion are inhibited strongly by trimethylsphingosine (TMS). The phenomenon could result from inhibition of 47 kDa protein phosphorylation or of phosphoinositide turnover as a membrane signaling pathway in platelets.

U.S. Pat. No. 5,137,919 teaches TMS, methods of making same and uses of same. U.S. Pat. No. 5,151,360 teaches another use of TMS.

SUMMARY OF THE INVENTION

One object of the invention is to provide TMS derivatives which retain TMS activities, such as inhibiting metastatic properties of malignant tumor cells.

Another object of the invention is to provide TMS derivatives and compositions thereof which inhibit protein kinase-C.

A further object of the invention is to provide TMS derivatives and compositions thereof for inhibiting platelet aggregation.

A fourth object of the invention is to provide TMS derivatives and compositions thereof for inhibiting inflammation.

A fifth object of the invention is to provide TMS derivatives for modulating cell adhesion molecule expression.

An sixth object of the invention is to provide TMS derivatives for treating thrombosis.

A seventh object of the invention is to provide TMS derivatives to serve as cell and tissue preservatives.

The and other objects have been attained by identifying those portions of the TMS molecule which affect the various activities of TMS. Those TMS derivatives can be made which enhance some or all of the known TMS activities and which enhance other characteristics of TMS which make TMS more suitable for treatment applications.

Among the activities of the parent compound, N,N,N-trimethylsphingosine, of interest are a higher inhibitory activity on protein kinase-C and metastatic potential of tumor cells than other sphingosine derivatives; inhibition of platelet aggregation and tumor-induced platelet interaction; inhibition of inflammatory processes; affects the expression of intercellular adhesion molecules; can be used as a tissue or cell preservative; and is water soluble. The known characteristics of TMS serve as the defining characteristics of a TMS derivative of the instant invention.

Those and other objects have been achieve in the development of TMS derivative of the formulae, (1) $CH_2OH$—$CH(NR_3)$—$CHOH$—$C(X)H_nY$, wherein R is an aliphatic hydrocarbon, provided that no more than two R groups are —$CH_3$; X is a single bond, double bond or a triple bond; wherein n=0 when X is a triple bond, n=1 when X is a double bond and n=2 when X is a single bond; and Y is a cyclic or aliphatic hydrocarbon and (2) $CH_2OH$—$CH(NR_3)$—$CH$=$CH$—$CHXY$, wherein R is an aliphatic hydrocarbon, provided that no more than two R groups are —$CH_3$; X is a group which mimics the C3 hydroxyl of sphingosine and Y is a cyclic or aliphatic hydrocarbon.

BRIEF DESCRIPTION OF THE FIGURE

FIG. 4 sets forth the scheme for making one of the intermediate structures. FIG. 5 depicts a scheme which uses the intermediate 3a of FIG. 4 to make another intermediate, structure 6b. FIG. 6 depicts a scheme using structure 6b to make the target compounds.

DETAILED DESCRIPTION OF THE INVENTION

Figure 1:
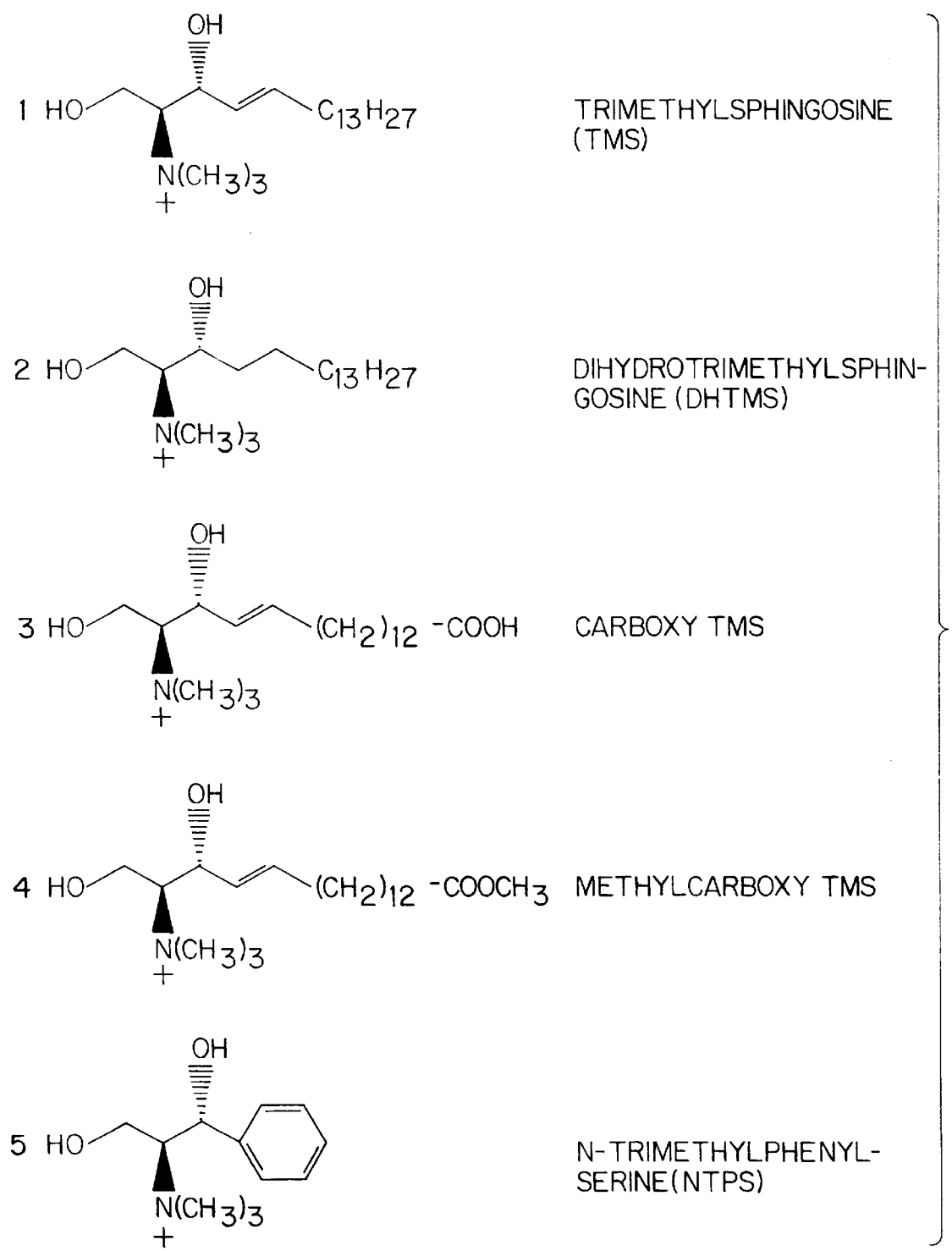
FIG. 1 depicts trimethylsphingosine and several derivatives thereof.

N,N,N-trimethylsphingosine (TMS) is highly water soluble, particularly at physiologic pH. Thus the compound has a distinct advantage over sphingosine, N-monomethylsphingosine (MMS) and N,N-dimethylsphingosine (DMS), which are less water soluble, as a modulator of cell processes.

As used herein, sphingosine indicates sphingosine irrespective of D- or L-, or erythro- or threo-configuration.

Also as used herein, "cells" include nucleated and anucleated structures. Thus, in addition to the 'classical' cells, such as lymphocytes and endothelial cells, biologic structures such as erythrocytes and platelets fall within the ambit of the term.

The terms, "analog" and "derivative" are considered synonymous.

Further as used herein, "synthetically prepared" means a product prepared from commercially available reagents and building blocks and assembled into sphingosine and derivatives thereof by chemical reaction in vitro. Otherwise, sphingosines are prepared from sphingolipids which occur naturally.

Because of the multi-functionalized nature of the parent molecule, sphingosine, direct quaternization by exhaustive methylation (Sommer et al., J. Org. Chem. 36, 824, 1971) or reductive methylation using aqueous formaldehyde ($CH_2O$/NaCNBH) is not always reproducible.

Alternatively, N,N,N-trimethylsphingosine can be prepared synthetically from commercially available unsubstituted reagents. For example, it is found that unsubstituted sphingosine (Sigma Chemical Company) can be derivatized to form (4E)-N,N-dimethyl-D-erythro-sphingosine by a known method (Igarashi et al. JBC, 265, 5385, 1990). The N,N-dimethylsphingosine so obtained undergoes quaternization in almost quantitative yield, see U.S. Pat. Nos. 5,137,919 and 5,151,360.

Briefly, about a 37% aqueous solution of formaldehyde (which is about 20 eq.) is added to a solution of D-erythro-sphingenine in acetate buffer (NaOAc—AcOH—$H_2O$, pH 4.5). The solution is mixed at room temperature for about 10 minutes and then sodium cyanoborohydride ($NaCNBH_3$—CN) is added three times (at about 3.0, 2.0 and 1.0 eq., respectively). Excess methanol, or a longer chain alcohol, is added sequentially at five minute intervals. The solution is concentrated under a nitrogen stream in an "N-EVAP" (Organomation Assoc., Inc., South Berlin, Mass.) and the compound extracted with chloroform.

The extract can be purified by high pressure thin layer chromatography using standard procedures. N,N-dimethylsphingosine prepared as described above using methanol is obtained as a colorless syrup in about 80% yield. The molecule has a formula weight of 329.3281 with a formula of $C_{20}H_{40}HNO_2$ as deduced from high resolution mass spectrometry.

Referring once again to DMS, DMS is dissolved in anhydrous chloroform. Freshly distilled iodomethane (a volume of about 170 µl, 2.73 m/mol), or longer chain iodoalkane, is added to the DMS solution and the mixture is stirred in the dark at ambient temperature. (The amount of excess iodomethane is not critical and amounts from 25 to 100% in excess produce satisfactory results.)

The reaction generally is complete in a few hours, although for convenience the mixture is allowed to stand overnight. Progress of the reaction can be monitored by thin layer chromatography (TLC) using a buffer comprising ethyl acetate:methanol:ammonium hydroxide in a ratio of 20:10:2. After incubation, the precipitated quaternary ammonium salt is diluted with water and then repeatedly extracted with chloroform (3 ml×4). The organic layer is dried over magnesium sulphate and then concentrated in vacuo. Practicing the above method, 37 mg (86% yield) of compound was obtained as yellow crystals.

The yellow crystals are dissolved with stirring in an aqueous suspension of preneutralized (pH=7.00) anion exchange resin (chloride form, Dowex 1×2-400, 500 mg) at room temperature for three hours. The mixture then is filtered through a sintered glass funnel and then freeze dried (8 millitorr for two days).

Practicing the above method, 26.5 mg (93% yield) of N,N,N-trimethylsphingosine chloride salt was obtained. The structure of the product was ascertained by proton nuclear magnetic resonance (500 MHz, $CDCl_3$) and found to contain nine hydrogen groups and a trimethyl derivatized amino group. $^1$H NMR ($D_2O$) δ0.88 (t, 3, J=6.8 Hz, Me), 1.31 (br s, 22, 11×C$\underline{H}_2$), 2.08 (q, 2, J=6.8 Hz, 2×H-6), 3.29 (s, 9 N$^+$Me$_3$), 3.38 (br s, 1, H-3), 4.13 (br s, 2, 2×H-1), 5.57 (dd, 1, J=3.1 and 3.4 Hz, H-4) and 5.90 (m, 1, H-5). The predicted molecular formula of the compound is $C_{21}H_{44}NO_2$ with an expected molecular weight of 342.3372 and mass spectroscopy revealed a formula weight of 342.3371 ($C_{21}H_{44}NO_2$, Δ−0.0003).

The effect of TMS derivatives on cell proliferation can be demonstrated in part by exposing various tumor cells to a compound of interest in vitro and in vivo.

An in vitro assay relying on tritiated thymidine incorporation can be used to ascertain the effect of various compounds on cell proliferation. Briefly, tumor cells are seeded in flat bottom 96 well plates (Corning, N.Y.) at a concentration of $2\times10^4$ cells per well. The cells were cultured for 2 days in DMEM containing various concentrations of sphingoid which was added as a PBS solution. The medium then was supplemented with tritiated thymidine at a concentration of 0.5 µCi per well. Following a six hour incubation the cells were collected using the PHD Cell Harvester (Cambridge Technology, Cambridge, Mass.) and amounts of incorporated radioactivity were determined after adding a suitable cell lysing agent and scintillation cocktail, such as ScintiVerse BD (Fisher Scientific, Fairlawn, Calif.) which performs both functions.

In another in vitro assay, the influence of various compounds on PK-C activity was monitored. Certain tumor cells present high levels of PK-C activity. The human epidermoid carcinoma cell line A-431 (ATCC No. CRL 1555) was used in a bioassay for PK-C activity as described in Igarashi et al. (supra). Briefly, phosphatidylserine (5 µg/tube) and 1,2-diolein (0.05 µg/tube), with or without an appropriate quantity of a sphingosine derivative sample, were added in an organic solvent, ethanol or ethanol/chloroform, to a 1.5 ml tube (Sarstedt) and the mixture was evaporated under a $N_2$ stream. The lipid mixture was sonicated in about 30 µl of 20 mM Tris-HCl (pH 7.5) for 30 minutes.

The resulting liposomes were supplemented with a buffer mixture comprising 25 mM Tris-HCl (pH 7.5), 10 mM $MgCl_2$, 400 AM EDTA, 50 µM EGTA, 500 µM $CaCl_2$, 200 4g/ml histone III-S or myelin basic protein and 20 µM $\gamma[^{32}P]$-ATP ($2\times10^6$ cpm) to a final volume of about 90 µl. The reaction was initiated by adding about 10 µl of PK-C, which was prepared from A431 cells as described in Igarashi et al. (supra) or from mouse brain as described in Kikkawa et al. (Biochem. Biophys. Res. Comm., 135, 636, 1986) and contained about 1–2 µg protein, and the mixture was incubated for ten minutes at 30° C. The reaction was terminated by the addition of 1 ml of a 1 mM ATP solution at pH 7.5 containing 25% TCA and 1% BSA.

The precipitate was collected by centrifugation, washed twice with 1 ml of 25% TCA, then dissolved in 1 ml of 1 M NaOH containing 0.1% deoxycholate with slight heating (80° C. for ten minutes) and counted in a scintillation counter. Reaction mixtures without phosphatidylserine, 1,2-diolein or $Ca^{2+}$ were used as controls. The bioassay used two different substrates, histone III-S and myelin basic protein.

Certain cancer cells show a higher metastatic potential and invasive capability than others. For example, in the mouse, the BL6 and F10 melanoma cell lines are highly metastatic and invasive. On the other hand, the F1 variant is much less metastatic and invasive (I. R. Hart et al., Amer. J. Pathol., 97, 587–592 (1979); G. Poote et al., Cancer Res. 42, 2770–2778 (1982); F1 and F10 clones from ATCC CRL 6323, and CRL 6475, respectively). BL6 and F1 cells were tested in vitro as described above. TMS was more effective than DMS and sphingosine at inhibiting cell growth. Also BL6 cells were more sensitive to TMS treatment as evidenced by the need for lower TMS concentrations.

BL6 cells were injected into mice and metastatic deposits in the lung were assessed after various treatments including route and timing, of administration. TMS is effective in suppressing lung colonization and tumor development irrespective of route or timing although early treatment is preferred and repeated treatment is more effective.

Another aspect of TMS derivatives is the profound effect thereof on platelet aggregation (for the purposes of the instant invention, platelets are considered cells). TMS derivatives inhibit platelet aggregation.

On thrombin stimulation, a 40 kD (or 47 kD) platelet protein is phosphorylated. TMS exposure inhibits phosphorylation of the 40 kD (or 47 kD) platelet protein. While not wanting to be bound by their statement, the inventors believe that absence of phosphorylated 40 kD (or 47 kD) protein prevents platelet aggregation.

Platelet activation is of central importance for initiation of numerous biological processes related to hemostasis, inflammation, wound healing and tumor cell metastasis and invasion. There are many factors and mechanisms which influence platelet activation and many consequences of activation. The selectin GMP-140 binds to neutrophils, HL60 cells or tumor cells which express sialosyl-$Le^x$. Mechanisms of expression of GMP-140 and its subsequent binding to sialosyl-$Le^x$ are of central importance for initiation of inflammatory processes as well as tumor cell metastasis. GMP-140 expression is down-regulated or blocked by preincubation with TMS.

The utility of TMS derivatives is not limited to the suppression of malignant cell growth. Inflammation is characterized in part by a proliferation of lymphoid and myeloid cells. Generally the proliferation serves a beneficial purpose, such as sequestration of foreign antigen or enhancement of restorative capabilities following an insult, but at times can occur abnormally, for example as a result of an autoimmune dysfunction.

Thus TMS derivatives have utility in controlling cell proliferation of apparently normal cells. Mouse CTLL-2 cells (ATCC No. TIB 214), a T lymphocyte cell line, were plated at $1.5\times10^4$ cells per well and exposed to test substances. Cell proliferation is monitored by thymidine incorporation.

The effect of TMS derivatives on cell adhesion molecules is evidenced by the inhibition of cell adhesion molecule expression by platelets. For example thrombin induces expression of GMP-140 in platelets. However, exposure of platelets to TMS inhibits GMP-140 expression. Thus, TMS derivatives will be useful in disorders that rely on cell adhesion molecule dependent-processes.

As noted above, GMP-140, as does ELAM-1, binds sialosyl-$Le^x$. Thus, TMS derivatives will find utility in preventing lymphocyte-endothelial cell adhesion and subsequent interactions between cells such as the development of an inflammatory state at a site of injury.

Key portions of the TMS molecule have been identified. Those key portions of TMS have an effect on one or more of the activities set forth hereinabove. Various modifications can be made at such key sites to enhance a specific activity or several activities. For example, the D-erythro configuration at carbons 2 and 3 (numbering beginning from that side of the molecule bearing the nitrogen) is preferred over the D-threo, L-threo and L-erythro configurations. However, the impact of the 3 hydroxyl group can be mimicked by a compound carrying a reactive group, such as a halogen, at the 5 position, as found in 5F-TMS.

The trimethyl substitution at the amine group is another critical portion of the TMS molecule. The methyl group of TMS serves as an electron donating group. Hence, other suitable electron donating groups can be substituted for the methyl group so long as the anionic character of the nitrogen atom is maintained. Thus, for example, one or more of the methyl groups can be replaced by a hydrocarbon group, such as, an aliphatic hydrocarbon, for example, an ethyl group, a propyl group, a butyl group, a pentyl group, a hexyl group and the like, provided that the electron donating group has a molecular weight greater than 1 and no more than two of the groups are methyl groups.

The parent TMS molecule carries a double bond at the $C_4$ position. While presence of the double bond is not essential for inhibition of PKC activity, the particular steric configuration provided by the $C_4$ double bond does have an impact on inhibition of metastasis and platelet aggregation. A triple bond at $C_4$ is effective for PK-C inhibition but not for metastasis inhibition. Accordingly, the positioning of the one or more double bonds has a bearing on one or several TMS activities.

In concert with the number and positioning of double bonds, the size of and configuration of the aliphatic backbone have a role in the TMS activities disclosed herein. Hence, the aliphatic chain may be a single chain, a branched chain or two chains may derive from the $C_4$ position.

Preferably, the aliphatic chain is non-polar or hydrophobic as it is known that a carboxyl or an ester group at the terminus of the aliphatic chain destroys certain TMS activities.

Figure 2:
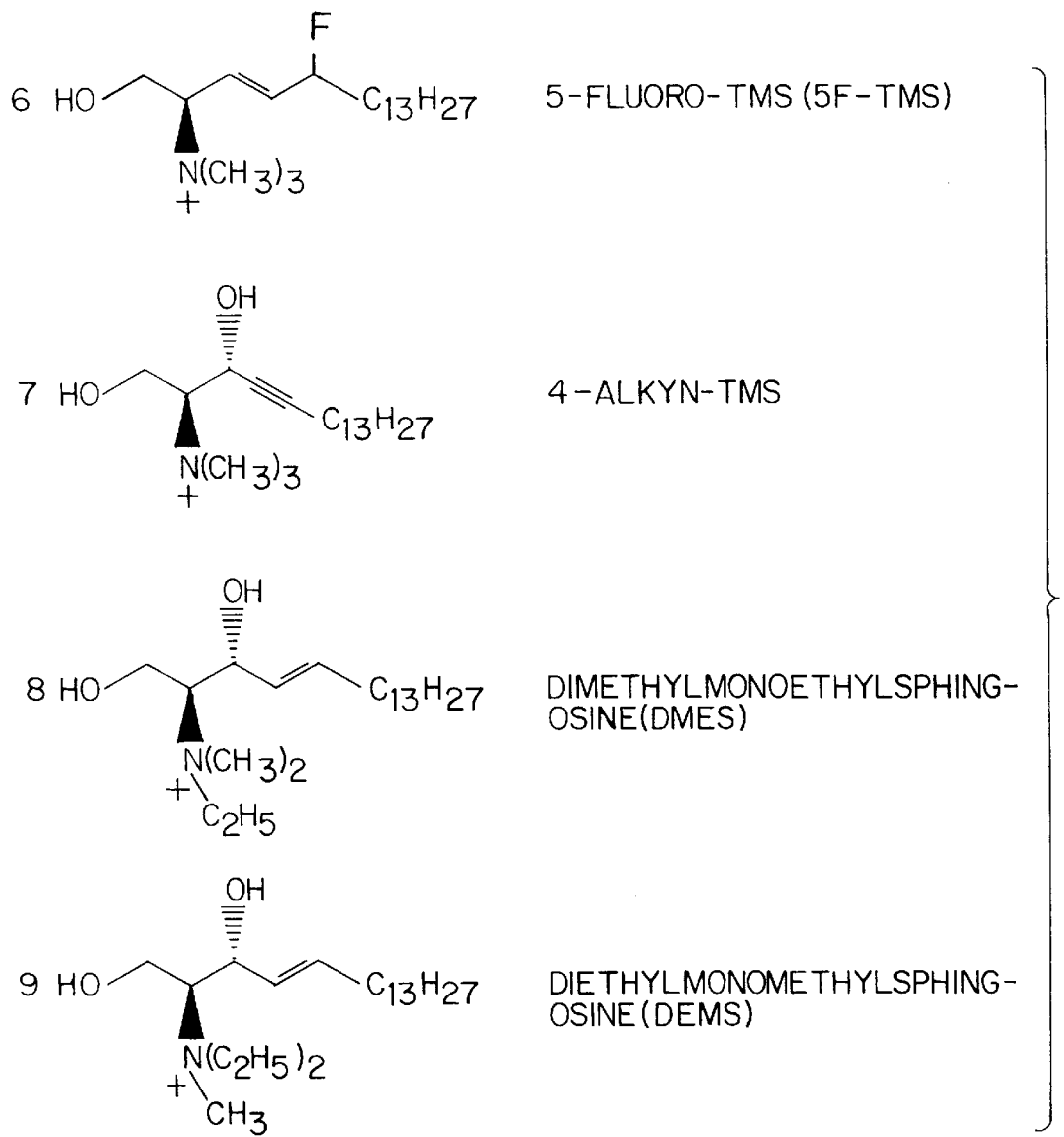
FIG. 2 depicts additional TMS derivatives.

Table I and FIGS. 1 and 2 set forth several TMS derivatives and activities thereof, the data of which in part defines the key portions of the TMS molecule. Hence, removal of the double bond separates activities. A carboxyl or a methylester group at the terminus of the aliphatic chain and lack of the aliphatic chain destroy certain TMS activities.

TABLE I

Effects of TMS derivatives on metastasis of B16BL6 melanoma cells

| TMS Derivative | Inhibition of metastasis | Inhiition of PA | PKC inhibition |
| --- | --- | --- | --- |
| TMS | +++ | +++ | +++ |
| DHTMS | +[2] | ++ | +++ |
| Carboxy TMS | −[3] | − | − |
| Methylcarboxy TMS | −[3] | − | − |
| NTPS | −[3] | − | − |
| 5F-TMS | +++ | +++ | +++ |
| 4-alkyn-TMS | + | ++ | +++ |

[1]Experimental and spontaneous metastasis with free derivative and liposomal formulation
[2]Experimental and spontaneous metastasis with liposomal formulation
[3]Pre-incubation with free derivative
+ effective
− not effective Various modifications can be made to the TMS molecule to obtain derivatives which substantially retain one or more TMS activities. Any such derivatives are contemplated to fall within the scope of the instant invention. Of particular interest are those derivatives that retain only a portion of the parent activities or have enhanced activities.

Some modifications can affect other properties, that is none of the specific activites described herein, of the molecule, such as serum half-life, solubility in aqueous media, stability of the compound, reduced side effects, enhanced cellular permeability and the like. Hence, other derivatives may present more desirable use characteristics that are directed to subsidiary charcteristics and properties.

The TMS derivatives of the instant invention can be made by known processes of organic sysnthesis based on and beginning with the synthetic scheme of TMS set forth hereinabove and directed to those key portions of the TMS molecule to enhance or isolate activities or to other portions of the TMS molecule to enhance subsidiary characteristics or to remove unwanted subsidiary characteristics.

For example, DHTMS can be prepared by the synthetic scheme set forth herein for making TMS except that the starting material is dihydrosphingosine, which is available commercially, for example, from Sigma.

TMPS can be obtained from phenylserine (Sigma) by the procedure described by Sommer (supra).

Figure 3:
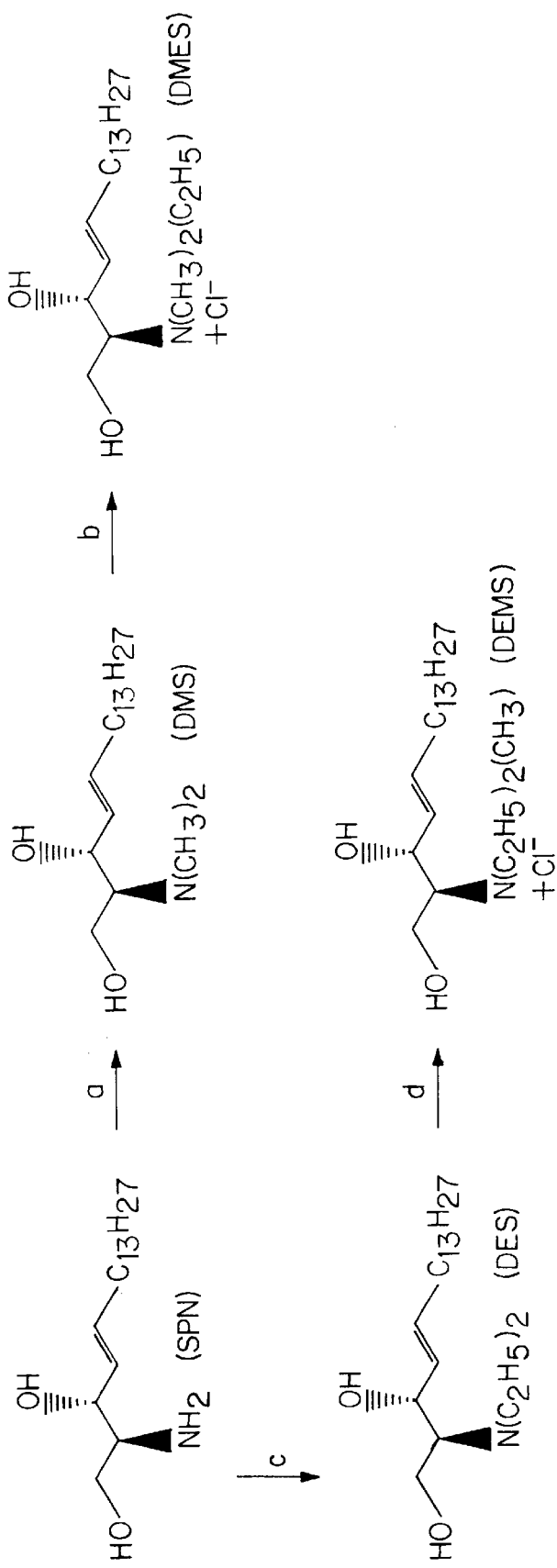
FIG. 3 depicts a synthetic scheme for making DMES and DEMS.
Figure 4:
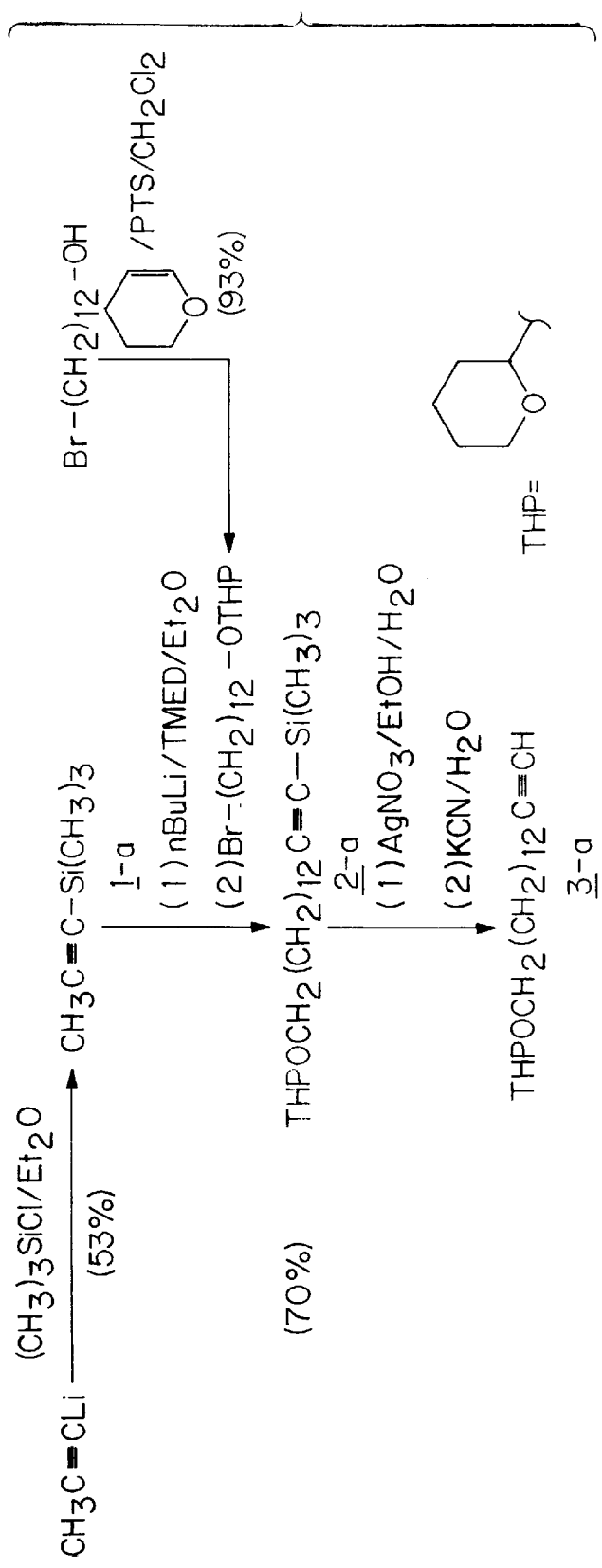
FIGS. 4–6 depict a synthetic scheme for making carboxy TMS and methylcarboxy TMS.
Figure 5:
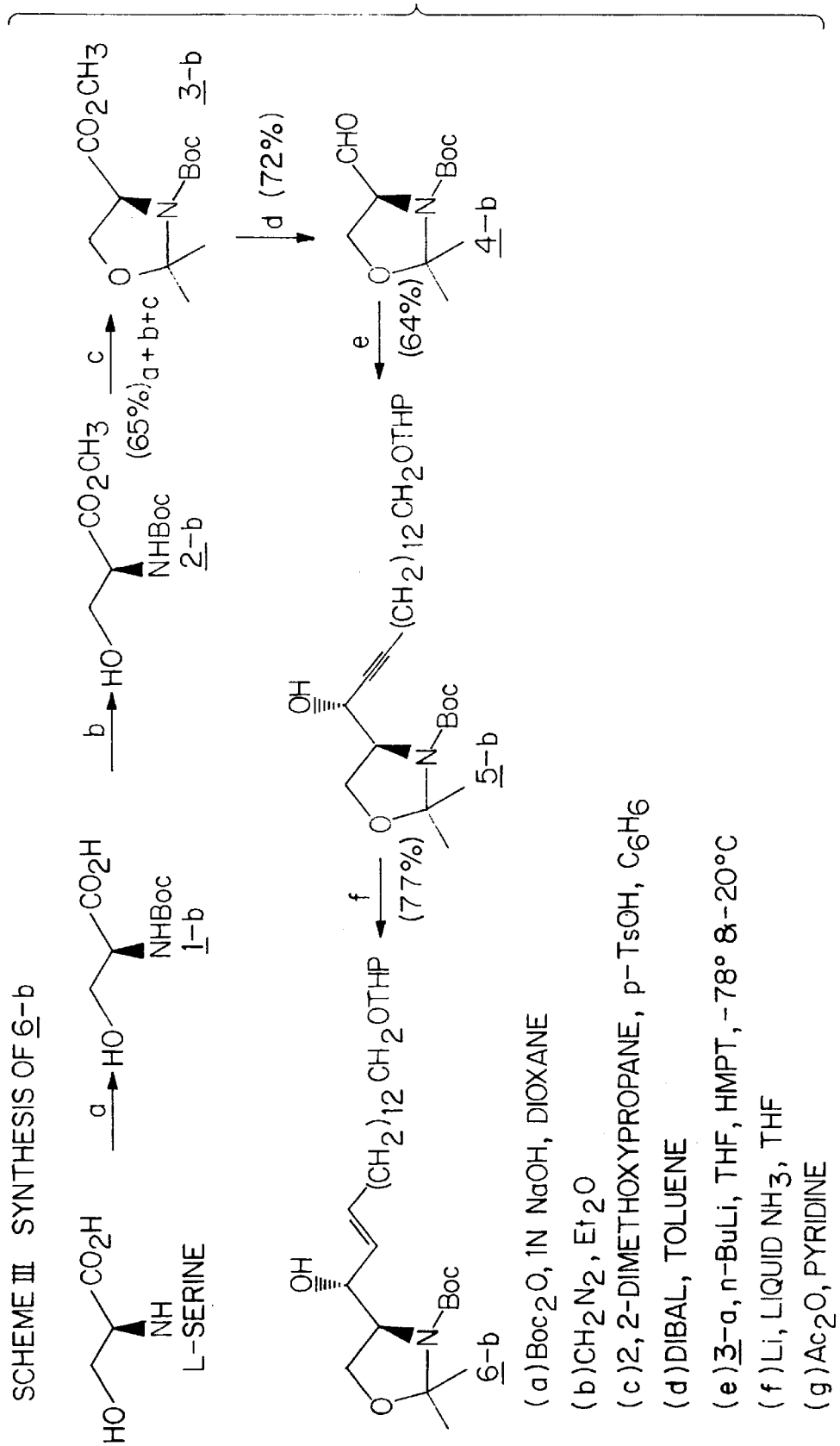
Figure 6:
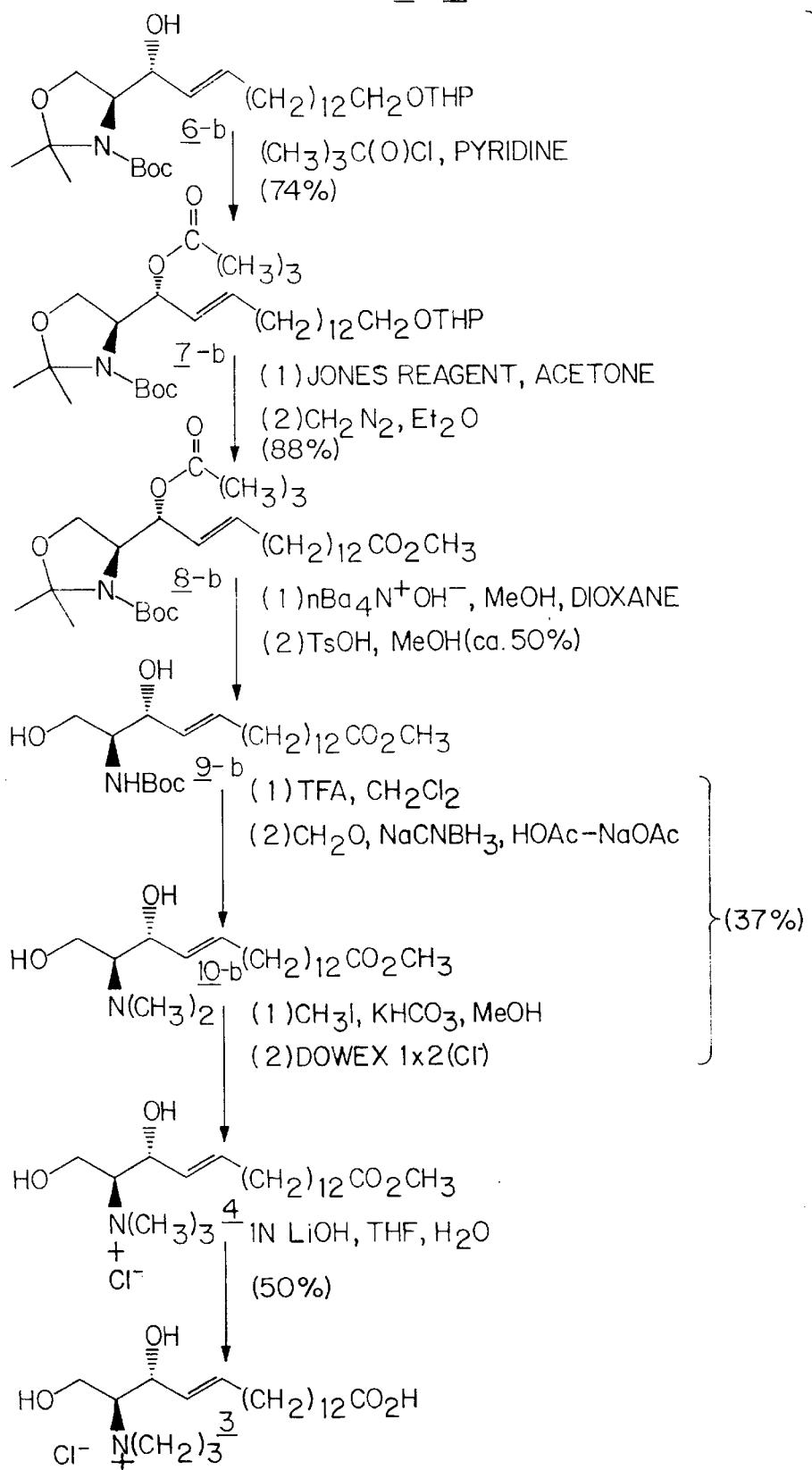
Figure 7:
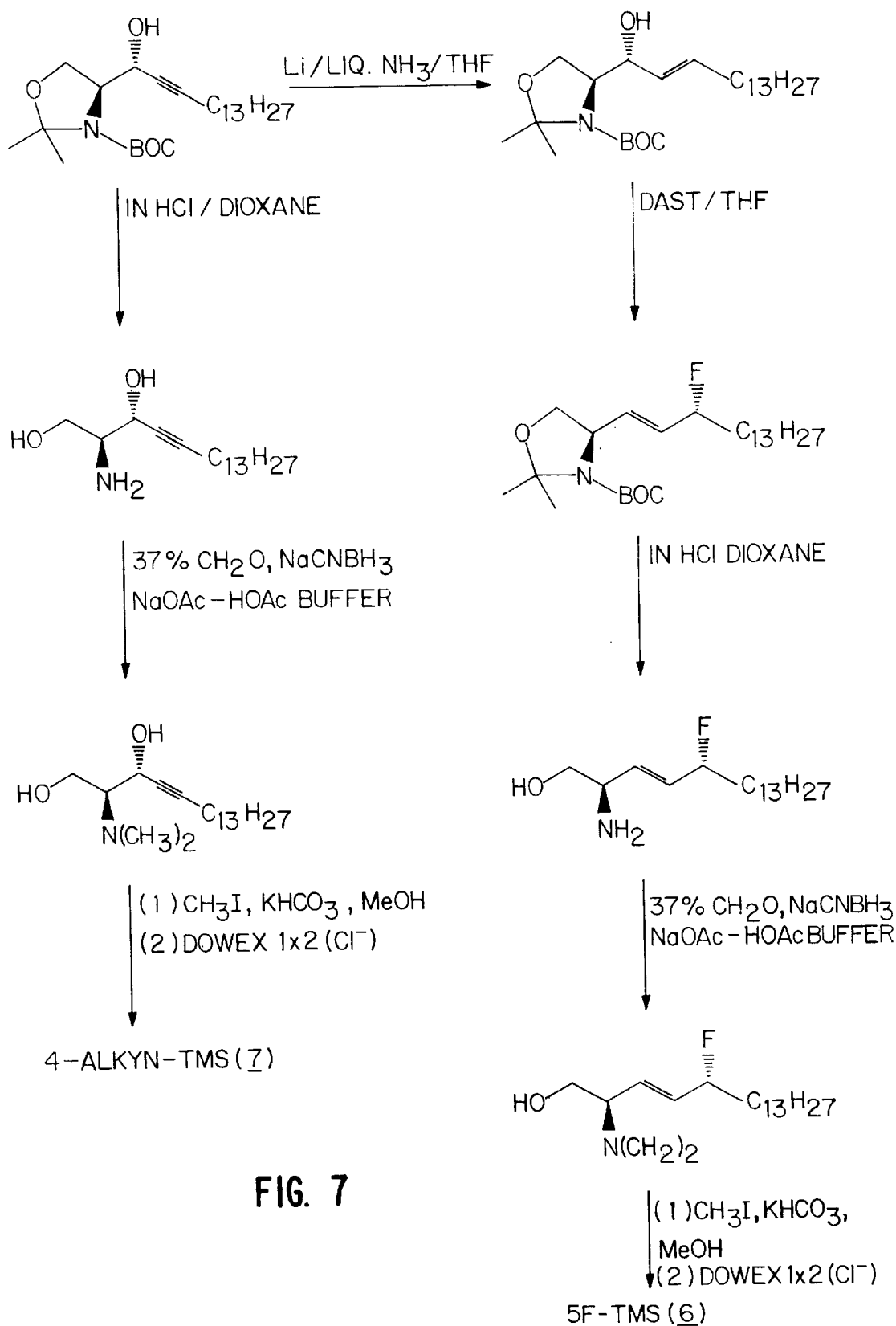
FIG. 7 sets forth synthetic schemes for making 5F-TMS and 4-alkyn-TMS.

A synthetic scheme for DMES and DEMS is set forth in FIG. 3. N,N-diethyl sphingosine was prepared in a fashion similar to the synthesis of DMS. DEMS and DMES can be obtained by the treatment of DES with $CH_3I$ and DMS with $C_2H_5I$ respectively. The reaction conditions are essentially the same as set forth hereinabove as to TMS except that the reaction can be conducted at a higher temperature and over a longer period of time to obtain suitable yields.

Because TMS derivatives have an inhibitory activity on protein kinase C and other kinases, TMS derivatives likely prevent the expenditure of intracellular ATP stores and hence dampen metabolic activity, in addition to the platelet aggregating inhibiting and cell adhesion inhibiting activities described herein. Thus, TMS derivatives can be used to preserve or to prolong storage of biologic materials, such as blood products.

For example, it has been shown that TMS retards erythrocyte metabolic activity in vitro under normal blood storage conditions as evidenced by a reduction of erythrocyte enzyme activity. Similar results can be expected for leukocytes and platelets.

Accordingly, TMS derivatives can be used as an adjunct to methods and formulations now in use for the preservation or storage of biologic materials, such as blood, blood components and organs awaiting transplantation. A cell growth inhibiting amount of TMS derivatives can be added to the storage medium.

Neutrophils (polymorphonuclear leukocytes) display three major agonist-dependent responses which normally are manifest in three major functions: (i) an exidative burst to produce superoxide ($O_2^-$); (ii) phagokinetic migratory activity; and (iii) the ability to interact with activated endothelial cells (EC's) and platelets. Mechanisms (ii) and (iii) result in adhesion to EC's and migration through the EC monolayer into the vascular or extravascular matrices. Normally, the functions collectively provide a useful mechanism for disposing of microorganisms in an inflammatory-type response. However, accumulation and overfunction of neutrophils during inflammatory disorders can result in tissue damage and circulatory disturbances.

Neutrophil responses are triggered by numerous stimuli, including chemotactic peptides, e.g., formyl-met-leu-phe (fMLP), arachidonate, lymphokines, such as IL-8, short-chain diacylglycerol (DAG) and phorbol esters (e.g., PMA).

Superoxide production in neutrophils obtained using art-recognized methods, for example, see Nojiri et al., Blood, 64, 534, 1984, as determined by reduction of cytochrome C, is inhibited by TMS in a dose-dependent manner. (The reduction of cytochrome C is monitored using known methods, such as the method of Clifford, Meth. Enz., 105, 393, 1981. $O_2$ consumption of neutrophils, as determined by electrical conductivity using an oxygen monitor and micro $O_2$ chamber assembly (Y.S.I. Inc., Yellow Springs, Ohio), is enhanced significantly by PMA. The PMA-dependent enhancement of $O_2$ consumption is inhibited strongly by TMS.

The phagokinetic activity of neutrophils on gold sol-coated plates can be determined by a technique essentially as taught in Albrecht-Buehler (Cell, 11, 395, 1977). Phagokinetic activity is suppressed significantly by TMS. The TMS-dependent inhibitory effect is reversed completely when the culture medium is replaced with TMS-free medium. Thus, the inhibitory effect of TMS on phagokinetic activity is not dependent on cytotoxicity.

A characteristic of neutrophils is the ability to adhere to activated EC's and to migrate through the EC monolayer into the vascular or extravascular matrix. The effect of TMS on neutrophil interactions with EC's and their subsequent trans-endothelial migration thereof can be monitored in vitro using human umbilical endothelial cells (HUVEC's) (Luscinskas et al., J. Imm., 146, 1617, 1991). Neutrophils are added to a HUVEC monolayer and neutrophil-HUVEC interactions are assessed microscopically following fixation, embedding and staining of monolayer sections.

Under physiological conditions, neutrophils are able to migrate into the collagenous matrix through the EC monolayer. When EC's are activated with IL-1β in M199 medium for 4 hours, neutrophils migrate into the collagenous matrix within 90 minutes. Neutrophil migration is inhibited strongly by pre-treatment of neutrophils with TMS.

When neutrophils, metabolically labeled with [$^{32}$P] sodium phosphate (2 mCi) for 1 hr to enrich intracellular ATP, are stimulated with 1.5 μM PMA, two protein bands following SDS-PAGE show greatly enhanced phosphorylation. The proteins have molecular weights of about 47 kDa and 65 kDa. When neutrophils are pre-incubated with 15–45 μM SPN, DMS or TMS and then stimulated with PMA, phosphorylation of both proteins is diminished significantly. The inhibitory effect on phosphorylation is observed within 2 minutes of incubation. Because phosphorylated 47 kDa and 65 kDa proteins appear to be direct substrates of PK-C, the inhibitory effects of SPN, DMS, and TMS may occur via an inhibitory effect on PK-C.

Metabolic incorporation of [$^{32}$P]sodium phosphate (4 mCi) into phosphatidylinositol (PI), phosphatidylinositol-4-phosphate (PIP) and phosphatidylinositol-4,5-bis-diphosphate (PIP2) is enhanced by chemotactic peptide fMLP (1 μM). The fMLP-dependent enhancement is suppressed strongly by pre-incubation of neutrophils with TMS.

The present invention further provides medicaments and treatments for affecting growth of human and animal cells and aggregation of human and animal platelets comprising:

(1) a therapeutically effective amount of an N,N,N-trimethylsphingosine derivative or pharmaceutically acceptable salts thereof; and (2) a pharmaceutically acceptable carrier, diluent or excipient.

The medicaments and methods are applicable both for in vitro and in vivo applications. Specific uses include treatment of malignancies, benign tumorous growths, inflammation, other manifestations of immune system dysfunction and when the immune system inappropriately or excessively responds to a stimulus.

The medicament comprises an effective amount of TMS derivative and a pharmaceutically acceptable carrier, diluent or excipient. The effective amount of a TMS derivative can be determined using art-recognized methods, such as by establishing dose-response curves in suitable animal models, such as described herein or in non-human primates, and extrapolating to human; extrapolating from suitable in vitro data, for example as described herein; or by determining effectiveness in clinical trials.

Suitable doses of medicaments of the instant invention depend upon the particular medical application, such as the severity of the disease, the weight of the individual, age of the individual half-life in circulation etc., and can be determined readily by the skilled artisan. The number of doses, daily dosage and course of treatment may vary from individual to individual.

TMS derivatives can be administered in a variety of ways such as orally, parenterally and topically. Suitable pharmaceutically acceptable carriers, diluents, or excipients for the medicaments of the instant invention depend upon the particular medical use of the medicament and can be determined readily by the skilled artisan. Also, the TMS derivatives can be delivered encapsulated within microspheres, such as liposomes, which can be made of phosphatidylcholine and cholesterol.

The medicament can take a variety of forms such as tablets, capsules, bulk or unit dose powders or granules; may be contained within liposomes; or may be formulated into solutions, emulsions, suspensions, ointments, pastes, creams, gels, foams or jellies. Parenteral dosage forms include solutions, suspensions and the like. The medicament is likely to contain any of a variety of art-recognized excipients, diluents, fillers etc. Such subsidiary ingredients include disintegrants, binders, lubricants, surfactants, emulsifiers, buffers, moisturizers, solubilizers and preservatives. The artisan can configure the appropriate formulation comprising TMS derivatives seeking guidance from numerous authorities and references such as, "Goodman & Gilman's, The Pharmaceutical Basis of Therapeutics" (6th ed., Goodman et al., eds., MacMillan Publ. Co., N.Y., 1980).

In body sites that are characterized by continual cell growth or require cell growth inhibition because of dysfunction and are relatively inaccessible, TMS derivatives can be administered in a suitable fashion to assure effective local concentrations. For example, TMS derivatives may be injected in a depot or adjuvant, carried in a surgically situated implant or reservoir that slowly releases a fixed amount of TMS derivatives over a period of time or may be complexed to recognition molecules with the capability of binding to the site presenting with abnormal cell growth. An example of such a contemplated scenario is a recognition molecule that is an antibody with binding specificity for a bone marrow specific antigen wherein said marrow specific antibody is complexed to a TMS derivative, said complex administered to a patient with leukemia.

Certain aspects of the invention are described in the following non-limiting Examples.

EXAMPLE 1

Platelets were isolated from platelet-rich plasma (purchased from the Oregon Red Cross, Portland, Oreg.). Contaminating erythrocytes were removed by centrifugation (80×g for 10 minutes). Platelets were obtained by centrifugation (300×g for 10 minutes), washed once in Tyrode buffer (pH 6.5) containing 22 mM trisodium citrate and 0.35% (w/v) BSA and resuspended in the same buffer to obtain a concentration of 1–2×10$^9$ platelets/ml. All procedures were performed at room temperature.

A suspension of platelets (about 3.5×10$^8$/ml) in Tyrode buffer was preincubated with inhibitor compounds (H-7 [1-(5-isoquinolinylsulfonyl)-2-methylpiperazine, a synthetic protein kinase-C inhibitor purchased from Seikagaku America Inc., St. Petersburg, Fla.], Calphostin-C [a synthetic protein kinase-C inhibitor obtained from Dr. Saitoh, Kyowa Hakko Co., Ltd., Machida, Tokyo, Japan], sphingosine [purchased from Sigma, St. Louis, Mo.] and dimethylsphingosine and trimethylsphingosine [synthesized according to Igarashi et al., Biochem., 28, 6796, 1989])

followed by addition of thrombin or ADP (both purchased from Sigma). Platelet aggregation was evaluated by transmittance change using an aggregometer (Chrono-log Corp., Havertown, Pa.) equipped with a computer analyzer.

EXAMPLE 2

GMP-140 expression was determined by (i) flow cytometry with mAb AC1.2, which is directed to GMP-140 and obtained from Dr. Furie (Tufts Univ. Sch. Med., Boston, Mass.) and (ii) adhesion of HL60 cells on platelet-coated solid phase.

A suspension of platelets ($1 \times 10^8$/ml) in Tyrode buffer was preincubated with inhibitor at pH 7.2, 37° C., for 5 minutes, then supplemented with activator, either thrombin (final concentration 1 U/ml) or phorbol 12-myristate 13-acetate (PMA) (final concentration $10^{-7}$ M), and then the mixture was incubated at 37° C. for 10 minutes. Platelets were fixed with an equal volume of 2% (w/v) paraformaldehyde in PBS and washed 2 times with PBS containing 1% (w/v) BSA.

The paraformaldehyde-fixed platelets were incubated with 50 $\mu$l of mAb AC1.2 (2.5 $\mu$g/ml) at room temperature for 30 minutes. Platelets were washed 2 times with PBS containing 1% (w/v) BSA, supplemented with 50 $\mu$l of fluorescein isothiocyanate-labeled goat anti-mouse Ig (purchased from Tago Co., Burlingame, Calif.), incubated at room temperature for 30 minutes and again washed 2 times with PBS containing 1% (w/v) BSA. As a negative control, the paraformaldehyde-fixed platelets were incubated with mouse IgG instead of mAb AC1.2 and treated as described above.

The platelets were analyzed in an Epics flow cytometer (Coulter Corp.) with suitable gating. To calculate the inhibitory effect of various reagents, the mean fluorescence intensity of resting platelets (obtained on incubation of platelets without activator) was subtracted from the value for the activated platelet sample.

TMS derivatives strongly inhibited GMP-140 expression.

EXAMPLE 3

HL60 (a human promyelocytic cell line available from the ATCC under accession number CCL 240) adhesion on resting or activated platelet-coated solid phase was evaluated as follows. Each well of a 48-well plate (Costar Scientific, Cambridge, Mass.) was filled with a poly-L-lysine solution (100 $\mu$g/ml in PBS) and incubated for 1 hour. Each well then was washed with PBS and then 150 $\mu$l of PBS containing $6 \times 10^7$ resting or activated platelets were added to each well and the plate was incubated for 1 hour. Plates were centrifuged (300×g for 7 minutes) and incubated a further 30 minutes at room temperature. Bound platelets were fixed by addition of 0.1% (w/v) glutaraldehyde in PBS for 2 minutes at 4° C. Each well was washed with 10 mM glycine in PBS and plates were incubated with 5% (w/v) BSA containing 0.1% (w/v) sodium azide, 10 mM glycine in PBS for 1 hour at room temperature.

After washing with culture medium (RPMI 1640 containing 5% (v/v) FCS), $1 \times 10^6$ HL60 cells labeled with [$^3$H]thymidine were added to each well. HL60 was maintained in RPMI 1640 medium (purchased from Irvine Scientific, Santa Ana, Calif.) supplemented with 10% FCS (Hyclone, Logan, Utah). (Radiolabeling of HL60 cells used for cell adhesion assays was performed by incubating cells with 2 $\mu$Ci/ml of [$^3$H]thymidine overnight.) After incubation for 45 minutes at room temperature, unbound cells were aspirated and wells were washed once with medium (RPMI 1640 containing 5% (v/v) FCS), bound cells were detached with 0.05% (w/v) trypsin-0.02% (w/v) EDTA (Irvine Scientific) in PBS and the levels of radioactivity in each well were determined in a liquid scintillation counter.

For both thrombin-stimulated and PMA-stimulated platelets, HL60 cell binding was inhibited strongly by TMS and DMS, but minimally inhibited by SPN. Binding of HL60 cells to activated platelets is considered to depend solely on recognition by GMP-140 of sialosyl-Le$^x$ expressed on HL60 cells since the binding was inhibited specifically by liposomes containing sialosyl-Le$^x$ but not by liposome containing other glycosphingolipids.

EXAMPLE 4

Human neutrophils were obtained from normal male adults. Heparinized peripheral blood was mixed gently with an equal amount of 1% dextran solution in PBS in a 60 ml injection syringe. The mixture was allowed to sit vertically for 60 to 90 minutes at 37° C. The upper phase, which is rich in white blood cells, was mounted gently on the same volume of Ficoll-Paque (Pharmacia LKB, Uppsala, Sweden) in Falcon 2095 plastic test tubes (Becton Dickinson Labware, Lincoln Park, N.J.). Centrifugation at 450g for 30 min at 4° C. brought the neutrophils to the bottom of the tubes. The upper phase and interface, which contains lymphocytes, were removed carefully by aspiration.

Contaminating erythrocytes were removed from the cell pellet by hypotonic lysis by resuspending the cell pellet in ice-cold distilled water for 30 sec then adding an equal volume of ice-cold 1.8% NaCl solution. After centrifugation at 80g for 10 min, the cells were resuspended with a suitable buffer or media.

The final preparation consisted of more than 98% neutrophils, as determined by Wright-Giemsa staining. The suspension was stored at 4° C. and used within 3 hr.

EXAMPLE 5

Freshly purified neutrophils ($\approx 8 \times 10^7$ cells) were preincubated at 37° C. with 2 mCi of Na$_2$H[$^{32}$P]O$_4$ in a buffer containing 0.1% lipid-free BSA-HEPES (10 mM pH 7.4, 136 mM NaCl, 4.9 mM KCl, 5.6 mM glucose and 0.33 mM CaCl$_2$) for 60 min in a shaking waterbath. Excess unbound components were removed by centrifugation and the pellets were resuspended in the same buffer, repeating twice. The cells then were divided into 7 treatment groups, each containing $\approx 1 \times 10^7$ cells in a total volume of 0.4 ml. TMS, SPN or DMS was added to a suspension and incubated at 37° C. for 10 min, followed by addition of PMA to a final concentration of 1.5 $\mu$M. Two minutes later, the reaction was terminated by adding 0.1 ml of Laemmli sample buffer and 20 mM EDTA, followed by heating at 100° C. for 5 min. Aliquots were separated through 10% sodium dodecyl sulfate gels using known procedures. $^{32}$P incorporation was visualized by autoradiography.

TMS had an affect on phosphorylation of specific proteins related to protein kinase C metabolism and activity.

All references cited herein are incorporated herein by reference.

While the invention has been described in detail and with reference to certain embodiments thereof, it would be apparent to one skilled in the art that various changes and modifications can be made without departing from the spirit and scope thereof.

What is claimed is:

1. A compound having the formula: CH$_2$OH—CH(NR$_3$)—CH=CH—CHXY; wherein R is an aliphatic hydrocarbon, provided that no more than two R groups are —CH₃; X is a group which mimics the C3 hydroxyl of sphingosine and Y is a cyclic or aliphatic hydrocarbon.

2. The compound of claim 1 wherein Y is an aliphatic hydrocarbon.

3. The compound of claim 1 wherein Y is an unsubstituted aliphatic hydrocarbon.

4. The compound of claim 1 wherein R is an alkyl group.

5. The compound of claim 4 wherein said alkyl group comprises one to six carbons.

6. The compound of claim 1 wherein X is a halogen.

* * * * *